United States Patent [19]

Lichtgarn

[11] 4,235,690
[45] Nov. 25, 1980

[54] TRACE GAS SENSOR

[76] Inventor: Fred Lichtgarn, 314 Evonshire St., Santa Barbara, Calif. 93111

[21] Appl. No.: 38,337

[22] Filed: May 11, 1979

[51] Int. Cl.$^3$ ............................................. G01N 27/46
[52] U.S. Cl. ................................. 204/195 R; 429/34
[58] Field of Search ...................... 429/13, 27, 69, 34; 204/1 B, 1 F, 1 N, 195 R

[56] References Cited

U.S. PATENT DOCUMENTS

| | | | |
|---|---|---|---|
| 567,959 | 9/1896 | Borchers | 429/13 |
| 901,012 | 10/1908 | Kitsee | 429/13 |
| 3,092,516 | 6/1963 | Rightmire | 429/13 |
| 3,115,427 | 12/1963 | Rightmire | 429/69 |
| 3,252,838 | 5/1966 | Huber et al. | 429/69 |
| 3,266,937 | 8/1966 | Lyons | 429/13 |
| 3,296,098 | 1/1967 | Arthur | 204/1 B |
| 3,649,505 | 3/1972 | Strickler et al. | 204/1 N |
| 3,959,087 | 5/1976 | Morrow | 204/1 B |
| 4,042,464 | 8/1977 | Blurton et al. | 204/1 N |
| 4,169,779 | 10/1979 | Tataria et al. | 204/1 F |

*Primary Examiner*—Donald L. Walton

[57] ABSTRACT

This invention directly converts some foreign trace gases that may be present in the air into an electrical current. Such gases include hydrogen sulphide, ammonia and chlorine. A rotating cylinder of glass, ceramic or plastic is coated on the outer surface with pure gold or pure platinum. This cylinder rotates, by external means, in a semi-enclosed chamber where the lower part of the cylinder extends out of the bottom of the chamber into a second chamber which contains an electrolyte which may be plain water. Thus, the cylinder as it rotates, is alternately exposed to gases in the first chamber and then to immersion in the water in the second chamber which contains an electrode. The cylinder itself is the other electrode. Any adsorbed trace gases on the cylinder wall will be immersed in water where the gases will become disassociated into ions. Some ions will remain on the cylinder wall and others will travel to the electrode in the water. If the cylinder is plated with gold the electrode must be gold also. The steady adsorption of gases and their breakdown into ions as the cylinder rotates results in a continuous electrical current that is easily measured.

2 Claims, 5 Drawing Figures

U.S. Patent
Nov. 25, 1980
4,235,690
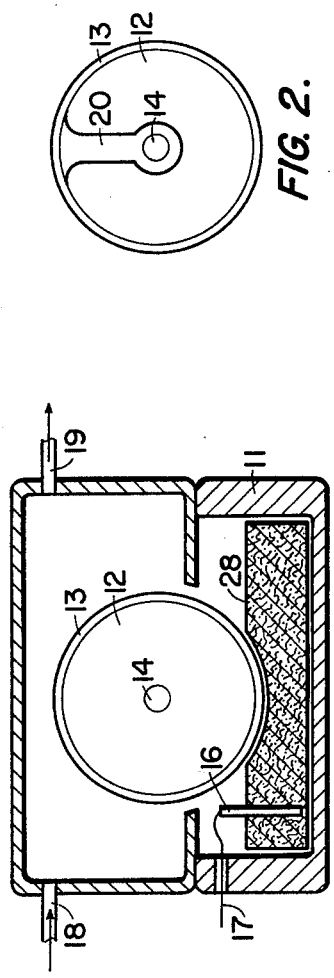
FIG. 2.
FIG. 3.
FIG. 1.
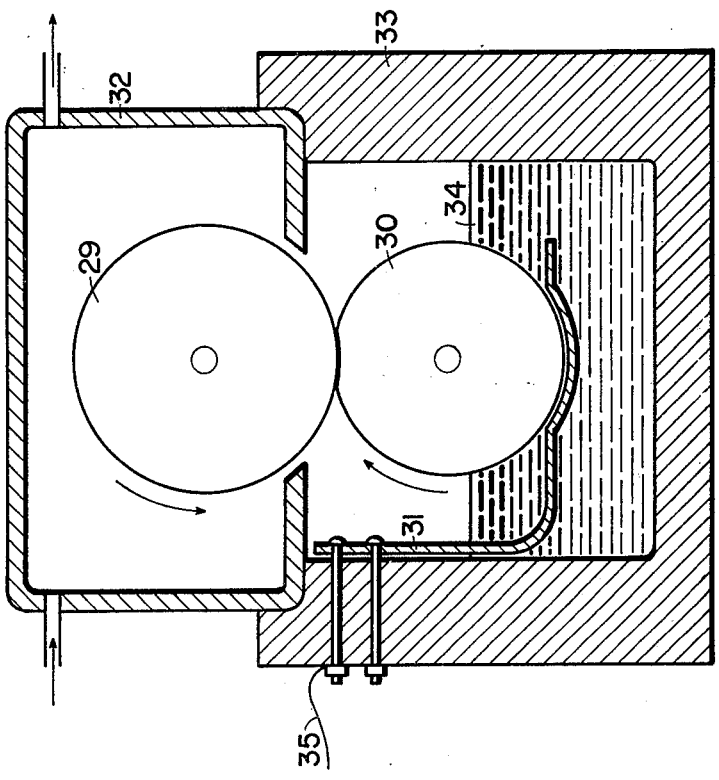
FIG. 5.
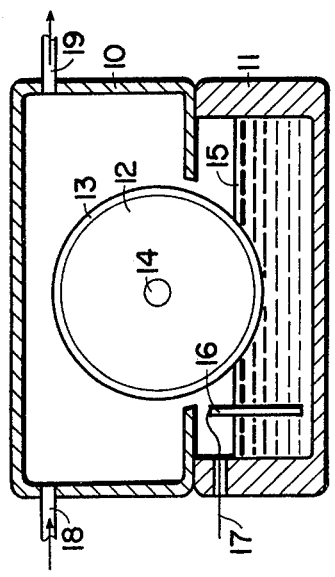
FIG. 4

TRACE GAS SENSOR

SUMMARY

I have found that some trace gases in the air will, by the adsorptive process, adhear onto the surface of clean metals. I prefer to use pure gold and pure platinum as they do not oxidize. When a metal with an absorbed foreign gas attached to it is immersed in water which has a second electrode in it a small electrical current is generated. This second electrode is made of the same metal as the first metal that absorbed gas. By having the first electrode made in a cylinder shape and rotated by external means a continouous electrical current is generated. If no trace gas is present there will be no current generated. If a trace gas is present there will be a reading in proportion. This invention has the advantage of being simple and reliable. Not all gases will convert to electricity. Gases like hydrogen sulphide, ammonia and chlorine can be easily detected. Gases are polarized differently.

FIG. 1 is a cross-section view showing the essential elements which are the two chambers and a cylinder.

FIG. 2 is an end view of the rotating cylinder.

FIG. 3 is a cross-section view of another embodiment.

FIG. 4 is a top view of FIG. 1 and FIG. 3.

FIG. 5 is a cross-section view of still another embodiment.

Referring to the drawings in FIG. 1 the upper chamber is 10. The lower chamber is 11. The rotating cylinder 12, is in this instance, made plastic glass or ceramic. The cylinder 12 as a metallic plating around it's circumference 13 to absorb foreign gases and to provide electrical contact. The shaft is 14. As cylinder 12 rotates it is immersed in electrolyte 15 where the absorbed gases disassociate into ions which travel to electrode 16 and wire 17. Electrolyte 15 may be just plain water-or it may be acidified or alkalized water; or it may some other liquid that can disassociate gases into ions. Chamber 10 has an inlet for gases 18 and where the gases with air is exhausted 19.

FIG. 2 shows the plated on electrical connector 20. It is made to connect the plated on surface 13 of cylinder 12 to shaft 14. Shaft 14 is metallic and connection with plated on connector 20 may be made by any well known means such as threading on shaft 14 and clamped by a nut. Plating 13 is shown much thicker than it really is for purposes of illustration. Non-metallic cylinders are used in this configuration because the cylinder is immersed into the electrolyte. A metal with a plating on it would give erroneous response as there would be two metals in the electrolyte.

FIG. 3 is exactly like FIG. 1 except there is no free liquid electrolyte. It is all absorbed into a felt or felt like pad 28 which lightly rubs onto cylinder 12. By using a felt pad the problem of accidental spillage is minimized.

FIG. 4 is a top view of FIG. 1 and FIG. 3. The top chamber is 10. The cylinder 12 rotates through opening 25. Shaft 14 is supported by bearings 24 and 26 at the required height. An insulating material block 22 supports frictional electrical contact 21 which rubs on shaft 14 and becomes wire lead 23. Cylinder 12 is rotated by external means through pulley 27.

FIG. 5 shows a method of using gas adsorbing cylinders that are not coated with gold or platinum. Cylinder 29 may be made of various stainless steels or titanium or nickel or of any similiar metals that do not oxidize easily. Carbon may be one possibility. A second cylinder 30 is made of a felt or felt like material and which has very finely divided diamond or alumina dust bonded to the felt. This is to prevent loss of the abrasive dust as cylinder 30 is slowly rotated. This abrasive dust will keep the surfaces of both the cylinder 29 and the water electrode 31 clean and effective. There will be little oxidation possible. Each cylinder is externally driven. Cylinder 29 and electrode 31 must each be made of exactly the same metals or the electric meter will not return to zero. Chamber 32 and 33 are similar to chambers 10 and 11. Electrolyte 35 may be water. Thus felt cylinder 30 is kept wet so that ions can travel to electrode 31. The top view of FIG. 5 would be very similar to FIG. 4.

REMARKS

It must be recorded that the cylinder may be made in different widths and shapes. For instance shape may be round as a ball. one test model had only about 15 inches of 0.007 platinum wire wound on a plastic disc. It detected gases perfectly. A wider width is shown so as to provide a stronger response.

Gold and platinum are not wetted by water. Water does not cling or otherwise cover the surface. Other metals, as far as I know do get wetted by water—at least to some degree—because of their inherent film of oxidation. Any oxidized surface would give unreliable response as the oxidized surface acts as an electrical insulator. This invention is not limited to a full 360 degree rotary motion in the cylinder exclusively. It may be rotated only 180 degrees one way and 180 degrees back again by suitable mechanical means. However it is simpler to have a full 360 degree continuous rotation. Rotating only 180 degrees is still, in my view, rotation. Chromium metal has good oxidation resistance. It will operate as well as the other non-precious metals.

Tantalum has rectifying properties that make instrument responsive to some gases and not responsive to others which may at times desireable.

I claim:

1. A gas sensing instrument operative to detect, measure and monitor trace amounts of foreign gases in the air, in the parts per million range, comprising: a rotatable cylindrical electrically conductive gas adsorbing first electrode, a chamber containing an electrolyte and a felt-like electrolyte absorbing material which is positioned as to contact the first said electrode, with a second electrode in said chamber contacting the said electrolyte and the said felt-like electrolyte absorbing material.

2. A gas sensing instrument operative to detect, measure and monitor trace amounts of foreign gases in the air, in the parts per million range, comprising: a rotatable cylindrical electrically conductive gas adsorbing first electrode, a chamber containing an electrolyte and a second electrode immersed in said electrolyte and containing a second rotatable cylinder of electrolyte absorbing felt-like material positioned between and in contact with said first and second electrodes, with the said second cylinder having a non-metallic finely divided and bonded abrasive coating for cleaning the electrically conductive surface of said first electrode when the said cylinders are rotated, whereby gas adsorbed on the said first cylindrical electrode and brought into contact with the electrolyte absorbed in the felt-like said second cylinder producing an ionic bridge between the said first and second electrodes.

* * * * *